United States Patent [19]

Hähnle et al.

[11] Patent Number: 6,136,873
[45] Date of Patent: Oct. 24, 2000

[54] WATER-ABSORBING, EXPANDED, CROSSLINKED POLYMERS, THE PRODUCTION AND USE THEREOF

[75] Inventors: Hans-Joachim Hähnle, Ludwigshafen; Manfred Walter, Speyer; Jürgen Tropsch, Römerberg; Gunnar Schornick, Neuleiningen; Thomas Anstock, Weisenheim, all of Germany

[73] Assignee: BASF Aktiengesellschaft, Ludwigshafen, Germany

[21] Appl. No.: 09/068,023

[22] PCT Filed: Oct. 25, 1996

[86] PCT No.: PCT/EP96/04644

§ 371 Date: May 4, 1998

§ 102(e) Date: May 4, 1998

[87] PCT Pub. No.: WO97/17397

PCT Pub. Date: May 15, 1997

[30] Foreign Application Priority Data

Nov. 3, 1995 [DE] Germany ............... 195 40 951

[51] Int. Cl.[7] .............................................. C08J 9/28
[52] U.S. Cl. ................... 521/62; 521/61; 521/63; 521/64
[58] Field of Search ................... 521/64, 61, 62, 521/63

[56] References Cited

U.S. PATENT DOCUMENTS

| | | |
|---|---|---|
| 4,394,930 | 7/1983 | Korpman . |
| 4,415,388 | 11/1983 | Korpman . |
| 4,529,739 | 7/1985 | Scott et al. . |
| 4,649,154 | 3/1987 | Dolman et al. . |
| 4,725,628 | 2/1988 | Garvey et al. . |
| 4,725,629 | 2/1988 | Garvey et al. . |
| 4,731,391 | 3/1988 | Garvey et al. . |
| 4,808,637 | 2/1989 | Boardman et al. . |
| 4,985,467 | 1/1991 | Kelly et al. . |
| 4,990,541 | 2/1991 | Nielsen et al. . |
| 5,328,935 | 7/1994 | Van Phan et al. ............... 521/64 |
| 5,338,766 | 8/1994 | Van Phan et al. ............... 521/64 |

FOREIGN PATENT DOCUMENTS

| | | |
|---|---|---|
| 0 421 264 A2 | 4/1991 | European Pat. Off. . |
| 0 427 219 A2 | 5/1991 | European Pat. Off. . |
| 2 136 813 | 9/1984 | United Kingdom . |
| WO 88/09801 | 12/1988 | WIPO . |
| WO 94/22502 | 10/1994 | WIPO . |
| WO 95/02002 | 1/1995 | WIPO . |

*Primary Examiner*—Morton Foelak
*Attorney, Agent, or Firm*—Oblon, Spivak, McClelland, Maier & Neustadt, P.C.

[57] ABSTRACT

Water-absorbing, expanded, crosslinked polymers obtainable by (I) foaming a polymerizable aqueous mixture which comprises (a) monoethylenically unsaturated monomers which contain acidic groups and are at least 50 mol % neutralized, (b) with or without other monoethylenically unsaturated monomers, (c) crosslinkers, (d) initiators, (e) 0.1–20% by weight of at least one surfactant, (f) with or without at least one solubilizer and (g) with or without thickeners, foam stabilizers, polymerization regulators, fillers and/or cell nucleating agents, where the foaming takes place by dispersing fine bubbles of a gas which is inert to free radicals, and (II) polymerizing the foamed mixture to form an expanded hydrogel and adjusting the water content of the expanded polymer to 1–45% by weight, a process for their production and their use in hygiene articles employed to absorb body fluids and in dressing material for covering wounds.

29 Claims, No Drawings

WATER-ABSORBING, EXPANDED, CROSSLINKED POLYMERS, THE PRODUCTION AND USE THEREOF

The invention relates to water-absorbing, expanded, crosslinked polymers, to a process for the production thereof and to the use thereof in hygiene articles employed to absorb body fluids and in dressing material for covering wounds.

Water-absorbing, crosslinked polymers are referred to as superabsorbents or superabsorbing polymers because they are able to absorb a multiple of their own weight of aqueous liquids to form hydrogels. Superabsorbents are used in practice, for example, in diapers for absorbing urine. The superabsorbents have the property of retaining the absorbed liquid even under mechanical stress.

In order to alter the use properties of superabsorbents, two different types of foams are known: (1) mixtures which contain superabsorbents in a foamed matrix, and (2) foams which consist of a superabsorbing material.

A foam belonging to category (1) is produced, for example, from a mixture which comprises, on the one hand, components for forming a polyurethane foam and, on the other hand, polymerizable monomers, a crosslinker and a polymerization initiator to produce a superabsorbent. The foam is formed from the polyurethane components in a mixture of this type in a polycondensation reaction and contains the superabsorbent which has been produced by polymerization of the monomers in the form of an interpenetrating network, cf. U.S. Pat. No. 4,725,628, U.S. Pat. No. 4,725,629 and U.S. Pat. No. 4,731,391.

U.S. Pat. No. 4,985,467 discloses a polyurethane foam which contains a chemically bonded superabsorbent. Also known are combinations of latex foams into which superabsorbing, fine-particle materials are incorporated after the foaming process, cf. EP-A-427 219 and U.S. Pat. No. 4,990,541.

Products belonging to category (2) of foams are those, for example, which are obtained by mixing a prefabricated superabsorbent in an extruder with a polyhydroxy compound and a blowing agent at elevated temperature. The foam is formed when the mixture is expelled from the extruder. Processes of this type are described, for example, in U.S. Pat. No. 4,394,930, U.S. Pat. No. 4,415,388 and GB-A-2 136 813.

U.S. Pat. No. 4,529,739 and U.S. Pat. No. 4,649,154 disclose processes for producing foams in which a water-swellable material having COOH groups is foamed with a blowing agent which liberates the blowing gas in a neutralization reaction with the COOH groups of the polymer.

According to the statements in WO-A 94/22502, superabsorbing foams based on crosslinked, partially neutralized polycarboxylates are produced by foaming a monomer mixture with a blowing agent which is insoluble in water and has a boiling point below 50° C., and completing polymerization of the foam at virtually the same time as the foaming.

EP-A-04 21 264 discloses the production of foam-like superabsorbents by polymerizing an aqueous monomer mixture which contains an emulsified oil phase. The action of the oil in this case is to occupy the space for the later pores in the foam and it is removed by evaporation, after the polymerization is complete, on drying the expanded material.

WO-A 88/09801 discloses that it is possible to process hydrophilic polymers, eg. sodium polyacrylate, in the presence of crosslinkers such as polyepoxides and blowing agents, by heating, to an expanded superabsorbent.

Another procedure known for producing expanded superabsorbents is to add carbonates, bicarbonates or carbon dioxide as blowing agents to a mixture of monomers which contain carboxyl groups, crosslinker and polymerization initiator, with the polymerization of the monomers being started at the same time as the addition of the blowing agent or shortly thereafter. The superabsorbent acquires a foam structure due to the carbon dioxide formed in the neutralization reaction, cf. U.S. Pat. No. 4,808,637. In the process disclosed in WO-A 95/02002, an expanded superabsorbent is mixed after production with one or more reactive compounds for subsequent surface crosslinking, and is heated to from 100 to 300° C.

In the processes described above for producing superabsorbing foams, the foam formation and the polymerization take place either synchronously or at negligibly different times. The foams which have not yet completely polymerized have only a short pot life, usually only a few minutes. It is a disadvantage in the processes indicated above that, for example, relatively large amounts of blowing agent are used, especially the CFCs used in the case of WO-A 94/22502.

It is an object of the present invention to provide expanded superabsorbents. It is another object of the present invention to indicate an improved process for producing expanded superabsorbents.

We have found that these objects are achieved by water-absorbing, expanded, crosslinked polymers obtainable by (I) foaming a polymerizable aqueous mixture which comprises
  (a) monoethylenically unsaturated monomers which contain acidic groups and are at least 50 mol % neutralized,
  (b) with or without other monoethylenically unsaturated monomers,
  (c) crosslinkers,
  (d) initiators,
  (e) 0.1–20% by weight of at least one surfactant,
  (f) with or without at least one solubilizer and
  (g) with or without thickeners, foam stabilizers, polymerization regulators, fillers and/or cell nucleating agents,
where the foaming takes place by dispersing fine bubbles of a gas which is inert to free radicals, and
(II) polymerizing the foamed mixture to form an expanded hydrogel and adjusting the water content of the polymer to 1–45% by weight.

The invention additionally relates to a process for producing water-absorbing, expanded, crosslinked polymers, which comprises foaming a polymerizable aqueous mixture of
  (a) monoethylenically unsaturated monomers which contain acidic groups and are at least 50 mol % neutralized,
  (b) with or without other monoethylenically unsaturated monomers,
  (c) crosslinker,
  (d) initiators,
  (e) 0.1–20% by weight of at least one surfactant,
  (f) with or without at least one solubilizer and
  (g) with or without thickeners, foam stabilizers, polymerization regulators, fillers and/or cell nucleating agents,
in a first stage by dispersing fine bubbles of a gas which is inert to free radicals, and polymerizing the resulting foam in a second stage to form an expanded hydrogel, and adjusting the water content of the expanded hydrogel to 1–45% by weight.

A polymerizable aqueous mixture is processed according to the invention to a foam which is stable to processing and can be molded as required. The polymerizable aqueous mixture comprises as components (a) monoethylenically unsaturated monomers which contain acidic groups and which are at least 50 mol% neutralized. Examples of monomers of this type are monoethylenically unsaturated $C_3$–$C_{25}$-carboxylic acids or anhydrides, for example acrylic acid, methacrylic acid, ethacrylic acid, α-chloroacrylic acid, crotonic acid, maleic acid, maleic anhydride, itaconic acid, citraconic acid, mesaconic acid, glutaconic acid, aconitic acid and fumaric acid.

Also suitable as group (a) monomers are monoethylenically unsaturated sulfonic acids, for example vinylsulfonic acid, allylsulfonic acid, sulfoethyl acrylate, sulfoethyl methacrylate, sulfopropyl acrylate, sulfopropyl methacrylate, 2-hydroxy-3-acryloxypropylsulfonic acid, 2-hydroxy-3-methacryloxypropylsulfonic acid, vinylphosphonic acid, allylphosphonic acid and 2-acrylamido-2-methylpropanesulfonic acid. The monomers can be used alone or mixed with one another to produce the superabsorbents. Group (a) monomers which are preferably used are acrylic acid, methacrylic acid, vinylsulfonic acid, acrylamidopropanesulfonic acid or mixtures of these acids, eg. mixtures of acrylic acid and methacrylic acid, mixtures of acrylic acid and acrylamidopropanesulfonic acid or mixtures of acrylic acid and vinylsulfonic acid.

The monomers are at least 50 mol % neutralized. Alkali metal bases or ammonia or amines are used, for example, for the neutralization. Sodium hydroxide solution or potassium hydroxide solution is preferably used for the neutralization. However, the neutralization can also be carried out with sodium carbonate, sodium bicarbonate, potassium carbonate or potassium bicarbonate or other carbonates or bicarbonates or ammonia. The acidic groups in the monomers are preferably at least 65 mol % neutralized.

The polymerizable aqueous mixture may, where appropriate, contain group (b) monomers. By these are meant other monoethylenically unsaturated monomers which are copolymerizable with monomers (a) and (c). These include, for example, the amides and nitriles of monoethylenically unsaturated carboxylic acids, eg. acrylamide, methacrylamide and N-vinylformamide, acrylonitrile and methacrylonitrile, dialkyldiallylammonium halides such as dimethyldiallylammonium chloride, diethyldiallylammonium chloride, allylpiperidinium bromide, N-vinylimidazoles such as N-vinylimidazole, 1-vinyl-2-methylimidazole and N-vinylimidazolines such as N-vinylimidazoline, 1-vinyl-2-methylimidazoline, 1-vinyl-2-ethylimidazoline or 1-vinyl-2-propylimidazoline, which can be used in the form of the free bases, in quaternized form or as salt in the polymerization. Also suitable are dialkylaminoalkyl acrylates and dialkylaminoalkyl methacrylates, eg. dimethylaminoethyl acrylate, dimethylaminoethyl methacrylate, diethylaminoethyl acrylate and diethylaminoethyl methacrylate. The basic esters are preferably used in quaternized form or as salt. Other suitable compounds of group (b) are, for example, vinyl esters of saturated $C_1$–$C_4$-carboxylic acids such as vinyl formate, vinyl acetate or vinyl propionate, alkyl vinyl ethers with at least 2 carbon atoms in the alkyl group, such as ethyl vinyl ether or butyl vinyl ether, esters of monoethylenically unsaturated $C_3$–$C_6$-carboxylic acids, eg. esters of monohydric $C_1$–$C_8$-alcohols and acrylic acid, methacrylic acid or maleic acid, monoesters of maleic acid, eg. monomethyl maleate, and hydroxyalkyl esters of said monoethylenically unsaturated carboxylic acids, eg. 2-hydroxyethyl acrylate, hydroxypropyl acrylate, hydroxybutyl acrylate, hydroxyethyl methacrylate, hydroxypropyl methacrylate and hydroxybutyl methacrylate, N-vinyllactams such as N-vinylpyrrolidone or N-vinylcaprolactam, acrylic and methacrylic esters of alkoxylated monohydric saturated alcohols, eg. of alcohols with 10 to 25 carbon atoms which have been reacted with 2 to 200 mol of ethylene oxide and/or propylene oxide per mol of alcohol, and monoacrylates and monomethacrylates of polyethylene glycol or polypropylene glycol, where the molecular weights ($M_N$) Of the polyalkylene glycols can be, for example, up to 2000. Other suitable group (b) monomers are alkyl-substituted styrenes such as ethylstyrene or tert-butylstyrene. The group (b) monomers can also be used in a mixture with the other monomers, eg. mixtures of vinyl acetate and 2-hydroxyethyl acrylate in any desired ratio, in the copolymerization.

The group (c) monomers have at least 2 ethylenic double bonds. Examples of monomers of this type, which are normally used as crosslinkers in polymerization reactions, are N,N'-methylenebisacrylamide, polyethylene glycol diacrylates and polyethylene glycol dimethacrylates which are derived in each case from polyethylene glycols with a molecular weight of from 106 to 8500, preferably 400 to 2000, trimethylolpropane triacrylate, trimethylolpropane trimethacrylate, ethylene glycol diacrylate, propylene glycol diacrylate, butanediol diacrylate, hexanediol diacrylate, hexanediol dimethacrylate, diacrylates and dimethacrylates of block copolymers of ethylene oxide and propylene oxide, polyhydric alcohols such as glycerol or pentaerythritol which are esterified two or three times with acrylic acid or methacrylic acid, triallylamine, tetraallylethylenediamine, divinylbenzene, diallyl phthalate, polyethylene glycol divinyl ethers of polyethylene glycols with a molecular weight of from 106 to 4000, trimethylolpropane diallyl ether, butanediol divinyl ether, pentaerythritol triallyl ether and/or divinylethyleneurea. Water-soluble crosslinkers are preferably used, eg. N,N'-methylenebisacrylamide, polyethylene glycol diacrylates and polyethylene glycol dimethacrylates derived from adducts of 2 to 400 mol of ethylene oxide and 1 mol of a diol or polyol, vinyl ethers of adducts of 2 to 400 mol of ethylene oxide and 1 mol of a diol or polyol, ethylene glycol diacrylate, ethylene glycol dimethacrylate or triacrylates and trimethacrylates of adducts of 6 to 20 mol of ethylene oxide and one mol of glycerol, pentaerythritol triallyl ether and/or divinylurea.

Also suitable as crosslinkers are compounds which contain at least one polymerizable ethylenically unsaturated group and at least one other functional group. The functional group in these crosslinkers must be able to react with the functional groups, essentially the carboxyl groups or sulfo groups, in the monomers (a). Examples of suitable functional groups are hydroxyl, amino, epoxy and aziridino groups.

Also suitable as crosslinkers are those compounds which have at least two functional groups able to react with carboxyl and sulfo groups in the group (a) monomers used. The suitable functional groups have already been mentioned above, ie. hydroxyl, amino, epoxy, isocyanate, ester, amide and aziridino groups. Examples of such crosslinkers are ethylene glycol, diethylene glycol, triethylene glycol, tetraethylene glycol, polyethylene glycol, glycerol, polyglycerol, propylene glycol, diethanolamine, triethanolamine, polypropylene glycol, block copolymers of ethylene oxide and propylene oxide, sorbitan fatty acid esters, ethoxylated sorbitan fatty acid esters, trimethylolpropane, pentaerythritol, polyvinyl alcohol, sorbitol, polyglycidyl ethers such as ethylene glycol diglycidyl ether, polyethylene glycol diglycidyl ether, glycerol diglycidyl ether, glycerol polyglycidyl ether, diglycerol polyglycidyl ether, polyglycerol polyglycidyl ether, sorbitol polyglycidyl ether, pentaerythritol polyglycidyl ether, propylene glycol diglycidyl ether and polypropylene glycol diglycidyl ether, polyaziridine compounds such as 2,2-bishydroxymethylbutanol tris[3-(1-aziridinyl)propionate], 1,6-hexamethylenediethyleneurea, 4,4'-methylenebis(phenyl)-N,N'-diethyleneurea, halo epoxy compounds such as epichlorohydrin and α-methylfluorohydrin, polyisocyanates such as 2,4-tolylene diisocyanate and hexamethylene diisocyanate, alkylene carbonates such as 1,3-di-oxolan-2-one and 4-methyl-1,3-dioxolan-2-one, polyquaternary amines such as condensates of dimethylamine with epichlorohydrin, homo- and copolymers of diallyldimethylammonium chloride, and homo- and copolymers of dimethylaminoethyl (meth)acrylate, which are, where appropriate, quaternized with, for example, methyl chloride.

Other suitable crosslinkers are polyvalent metal ions able to form ionic crosslinks. Examples of such crosslinkers are magnesium, calcium, barium and aluminum ions. These crosslinkers are added, for example, as hydroxides, carbonates or bicarbonates to the aqueous polymerizable solution.

Other suitable crosslinkers are multifunctional bases which are likewise able to form ionic crosslinks, for example polyamines or their quaternized salts. Examples of polyamines are ethylenediamine, diethylenetriamine, triethylenetetramine, tetraethylenepentamine, pentaethylenehexamine and polyethyleneimines, and polyvinylamines with molecular weights of up to 4,000,000 in each case.

In a preferred embodiment of the invention, two different crosslinkers are used, one of which is soluble in water and the other is insoluble in water. The hydrophilic crosslinker which is soluble in the aqueous phase of the reaction mixture produces, in a conventional way, a relatively uniform crosslinking of the resulting polymer, as is conventional in the production of a superabsorbent. The hydrophobic crosslinker which is insoluble or has only limited solubility in the polymerizable aqueous mixture concentrates in the surfactant interlayer between the gas phase and the polymerizable aqueous phase. This means that, in the subsequent polymerization, the surface of the foam is more extensively crosslinked than is the interior of the superabsorbent hydrogel. This results in a core/shell structure of the foam directly in the production of the superabsorbent foam. Such extensive surface crosslinking of a superabsorbent foam is possible in the prior art production processes only by subsequent surface crosslinking of an expanded superabsorbent which has already been formed. In the conventional procedure, a separate process step is necessary for this subsequent crosslinking, but this can be omitted in the process of the present invention.

Products according to the invention with a core/shell structure show distinctly improved properties compared with homogeneously crosslinked samples in respect of the absorption speed, distributing effect and gel stability. Apart from polyvalent metal ions, all the water-insoluble crosslinkers which are described above and can be assigned to the various groups are suitable for producing foams with a core/shell structure, ie. foams in which the entire surface is more highly crosslinked than the layer underneath, which has been referred to above as the core layer. Particularly preferred hydrophobic crosslinkers are diacrylates or dimethacrylates or divinyl ethers of alkanediols with 2 to 25 carbon atoms (branched, linear, with any suitable arrangement of OH groups) such as 1,3-propanediol, 1,4-butanediol, 1,6-hexanediol, neopentyl glycol, 1,9-nonanediol or 1,2-dodecanediol, di-, tri- or polypropylene glycol diacrylates or dimethacrylates, allyl acrylate, allyl methacrylate, divinylbenzene, glycidyl acrylate or glycidyl methacrylate, allyl glycidyl ether and bisglycidyl ethers of the alkanediols listed above.

Examples of suitable hydrophilic crosslinkers are N,N'-methylenebisacrylamide, polyethylene glycol diacrylates or dimethacrylates with a molecular weight $M_N$ of from 200 to 4000, divinylurea, triallylamine, diacrylates or dimethacrylates of adducts of from 2 to 400 mol of ethylene oxide and 1 mol of a diol or polyol or the triacrylate of an adduct of 20 mol of ethylene oxide and 1 mol of glycerol and vinyl ethers of adducts of from 2 to 400 mol of ethylene oxide and 1 mol of a diol or polyol.

The group (a) monomers are present in the polymerizable aqueous mixture in amounts of, for example, from 10 to 80, and preferably 20 to 60, % by weight. The group (b) monomers are used only where appropriate for modifying the superabsorbent foams and can be present in amounts of up to 50, preferably in amounts of up to 20, % by weight in the polymerizable aqueous mixture. The crosslinkers (c) are present in the reaction mixture in amounts of, for example, from 0.001 to 5, and preferably from 0.01 to 2, % by weight.

The polymerization initiators which can be used are all initiators which form free radicals under the polymerization conditions and which are normally used in the preparation of superabsorbents. It is also possible to initiate the polymerization by the action of electron beams on the polymerizable aqueous mixture. However, the polymerization can also be started in the absence of initiators of the abovementioned type by the action of high-energy radiation in the presence of photoinitiators.

Polymerization initiators which can be used are all compounds which decompose to free radicals under the polymerization conditions, eg. peroxides, hydroperoxides, hydrogen peroxide, persulfates, azo compounds and the redox catalysts. Water-soluble initiators are preferably used. It is advantageous in some cases to use mixtures of various polymerization initiators, eg. mixtures of hydrogen peroxide and sodium or potassium peroxydisulfate. Mixtures of hydrogen peroxide and sodium peroxydisulfate can be used in any desired ratio. Examples of suitable organic peroxides are acetylacetone peroxide, methyl ethyl ketone peroxide, tert-butyl hydroperoxide, cumene hydroperoxide, tert-amyl perpivalate, tert-butyl perpivalate, tert-butyl perneohexanoate, tert-butyl perisobutyrate, tert-butyl per-2-ethylhexanoate, tert-butyl perisononanoate, tert-butyl permaleate, tert-butyl perbenzoate, di(2-ethylhexyl) peroxydicarbonate, dicyclohexyl peroxydicarbonate, di(4-tert-butylcyclohexyl) peroxydicarbonate, dimyristyl peroxydicarbonate, diacetyl peroxydicarbonate, allyl peresters, cumyl peroxyneodecanoate, tert-butyl per-3,5,5-trimethylhexanoate, acetyl cyclohexylsulfonyl peroxide, dilauroyl peroxide, dibenzoyl peroxide and tert-amyl perneodecanoate. Particularly suitable polymerization initiators are water-soluble azo initiators, eg. 2,2'-azobis(2-amidinopropane) dihydrochloride, 2,2'-azobis(N,N'-dimethyleneisobutyramidine) dihydrochloride, 2-(carbamoylazo)isobutyronitrile, 2,2'-azobis[2-(2-imidazolin-2-yl)propane] dihydrochloride and 4,4'-azobis (4-cyanovaleric acid). Said polymerization initiators are used in conventional amounts, eg. in amounts of from 0.01 to 5, preferably 0.1 to 2.0, % of the weight of the monomers to be polymerized.

Also suitable as initiators are redox catalysts. The redox catalysts contain as oxidizing component at least one of the abovementioned peroxy compounds and as reducing component, for example, ascorbic acid, glucose, sorbose, ammonium or alkali metal bisulfite, sulfite, thiosulfate, hyposulfite, pyrosulfite or sulfide, metal salts such as iron(II) ions or silver ions, or sodium hydroxymethylsulfoxylate. The reducing component preferably used in the redox catalyst is ascorbic acid or sodium sulfite. Based on the amount of monomers used in the polymerization, for example, from $3\times10^{-6}$ to 1 mol % of the reducing component of the redox catalyst system and from 0.001 to 5.0 mol % of the oxidizing component of the redox catalyst are used.

If the polymerization is initiated by the action of high-energy radiation, photoinitiators are normally used as initiator. These may be, for example, a-splitters, H-abstracting systems or else azides. Examples of initiators of these types are benzophenone derivatives such as Michler's ketone, phenanthrene derivatives, fluorene derivatives, anthraquinone derivatives, thioxanthone derivatives, coumarin derivatives, benzoin ethers and derivatives thereof, azo compounds like the free-radical formers mentioned above, substituted hexaarylbisimidazoles or acylphosphine oxides. Examples of azides are: 2-(N,N-dimethylamino) ethyl 4-azidocinnamate, 2-(N,N-dimethylamino)ethyl-4-azidonaphthyl ketone, 2-(N,N-dimethylamino)ethyl 4-azidobenzoate, 5-azido-1-naphthyl 2-(N,N-dimethylamino)ethyl sulfone, N-(4-sulfonylazidophenyl) maleimide, N-acetyl-4-sulfonylazidoaniline, 4-sulfonylazido-aniline, 4-azidoaniline, 4-azidophenacyl bromide, p-azidobenzoic acid, 2,6-bis(p-azidobenzylidene) cyclohexanone and 2,6-bis(p-azidobenzylidene)-4-methylcyclohexanone. The photoinitiators are, if employed, normally used in amounts of from 0.01 to 5% of the weight of the monomers to be polymerized.

The polymerizable aqueous mixtures contain as component (e) from 0.1 to 20% by weight of at least one surfactant. The surfactants are of crucial importance for the production and stabilization of the foam. Anionic, cationic or nonionic surfactants or mixtures of surfactants which are compatible with one another can be used. It is possible to employ low molecular weight or else polymeric surfactants, and combinations of different or else similar types of surfactants have proved to be advantageous. Examples of nonionic surfactants are adducts of alkylene oxides, in particular ethylene oxide, propylene oxide and/or butylene oxide, and alcohols, amines, phenols, naphthols or carboxylic acids. Surfactants advantageously used are adducts of ethylene oxide and/or propylene oxide and alcohols containing at least 10 carbon atoms, where the adducts contain from 3 to 200 mol of ethylene oxide and/or prop-ylene oxide per mol of alcohol. The adducts contain the alkylene oxide units in the form of blocks or in random distribution. Examples of nonionic surfactants are the adducts of 7 mol of ethylene oxide and 1 mol of tallow fatty alcohol, products of the reaction of 9 mol of ethylene oxide with 1 mol of tallow fatty alcohol and adducts of 80 mol of ethylene oxide and 1 mol of tallow fatty alcohol. Other commercial nonionic surfactants consist of products of the reaction of oxo alcohols or Ziegler alcohols with 5 to 12 mol of ethylene oxide per mol of alcohol, in particular with 7 mol of ethylene oxide. Other commercial nonionic surfactants are obtained by ethoxylation of castor oil. For example, from 12 to 80 mol of ethylene oxide are added on per mol of castor oil. Further commercial products are, for example, the products of the reaction of 18 mol of ethylene oxide with 1 mol of tallow fatty alcohol, the adducts of 10 mol of ethylene oxide and 1 mol of a $C_{13}/C_{15}$ oxo alcohol, or the products of the reaction of 7 to 8 mol of ethylene oxide and 1 mol of a $C_{13}/C_{15}$ oxo alcohol. Other suitable nonionic surfactants are phenol alkox-ylates such as p-tert-butylphenol which has been reacted with 9 mol of ethylene oxide, or methyl ethers of products of the reaction of 1 mol of a $C_{12}$–$C_{18}$-alcohol and 7.5 mol of ethylene oxide.

The nonionic surfactants described above can be converted, for example, by esterification with sulfuric acid into the corresponding sulfuric acid half esters. The sulfuric acid half esters are employed as anionic surfactants in the form of the alkali metal or ammonium salts. Examples of suitable anionic surfactants are alkali metal or ammonium salts of sulfuric acid half esters of adducts of ethylene oxide and/or propylene oxide and fatty alcohols, alkali metal or ammonium salts of alkylbenzenesulfonic acid or of alkylphenol ether sulfates. Products of said type are commercially available. Examples of commercial anionic surfactants are the sodium salt of a sulfuric acid half ester of a $C_{13}/C_{15}$ oxo alcohol which has been reacted with 106 mol of ethylene oxide, the triethanolamine salt of dodecylbenzenesulfonic acid, the sodium salt of alkylphenol ether sulfates and the sodium salt of the sulfuric acid half ester of a product of the reaction of 106 mol of ethylene oxide with 1 mol of tallow fatty alcohol. Other suitable anionic surfactants are sulfuric acid half esters of $C_{13}/C_{15}$ oxo alcohols, paraffin-sulfonic acids such as $C_{15}$-alkylsulfonate, alkyl-substituted benzenesulfonic acids and alkyl-substituted naphthalene-sulfonic acids such as dodecylbenzenesulfonic acid and di-n-butylnaphthalenesulfonic acid, and fatty alcohol phosphates such as $C_{15}/C_{18}$ fatty alcohol phosphate. The polymerizable aqueous mixture may contain combinations of a nonionic surfactant and an anionic surfactant or combinations of nonionic surfactants or combinations of anionic surfactants. Cationic surfactants are also suitable. Examples thereof are the products, quaternized with dimethyl sulfate, of the reaction of 6.5 mol of ethylene oxide with 1 mol of oleylamine, distearyldimethylammonium chloride, laurylt-rimethylammonium chloride, cetylpyridinium bromide and the triethanolamine ester of stearic acid which is quaternized with dimethyl sulfate and is preferably used as cationic surfactant.

The surfactant content of the polymerizable aqueous mixture is 0.1 to 20, preferably 0.5 to 10, % by weight. In most cases, the polymerizable aqueous mixtures have a surfactant content of from 1.5 to 6% by weight.

The polymerizable aqueous mixtures may contain as component (f), where appropriate, at least one solubilizer. By this are meant water-miscible organic solvents, eg. alcohols, glycols, polyethylene glycols and monoethers derived therefrom, the monoethers containing no double bonds in the molecule. Suitable ethers are methylglycol, butylglycol, butyldiglcyol, methyldiglycol, butyltriglycol, 3-ethoxy-1-propanol and glycerol monomethyl ether.

The polymerizable aqueous mixtures contain 0 to 50% by weight of at least one solubilizer. If solubilizers are used, their content in the polymerizable aqueous mixture is preferably up to 25% by weight.

The polymerizable aqueous mixture may, where appropriate, contain thickeners, foam stabilizers, polymerization regulators, fillers and cell nucleating agents. Thickeners are used, for example, to optimize the foam structure and to improve the foam stability. This results in only slight shrinkage of the foam during the polymerization. Suitable thickeners are all natural and synthetic polymers which are known for this purpose and which greatly increase the viscosity of an aqueous system. These may be water-swellable or water-soluble synthetic and natural polymers. Superabsorbents in powder form are also suitable as thickeners.

A detailed review of thickeners is to be found, for example, in the publications by R. Y. Lochhead and W. R. Fron, Cosmetics & Toiletries, 108, 95–135 (May 1993) and M. T. Clarke, "Rheological Additives" in D. Laba (Ed.) "Rheological Properties of Cosmetics and Toiletries", Cosmetic Science and Technology Series, Vol. 13, Marcel Dekker Inc., New York 1993.

Water-swellable or water-soluble synthetic polymers suitable as thickeners are, for example, high molecular weight polymers of the monoethylenically unsaturated monomers which contain acidic groups described above under (a). Examples of thickeners of this type are high molecular weight homopolymers of acrylic acid and/or methacrylic acid or slightly crosslinked copolymers of acrylic acid and/or methacrylic acid and a compound which contains at least 2 ethylenic double bonds, eg. butanediol diacrylate. Also suitable are high molecular weight polymers of acrylamide and methacrylamide or copolymers of acrylic acid and acrylamide with molecular weights of more than 1 million. Copolymers of this type are known as thickeners. Other known thickeners are high molecular weight polyethylene glycols or copolymers of ethylene glycol and propylene glycol, and high molecular weight polysaccharides such as starch, gum guar, locust bean gum or derivatives of natural substances such as carboxymethylcellulose, hydroxyethylcellulose, hydroxymethylcellulose, hydroxypropylcellulose and cellulose mixed ethers. Another group of thickeners comprises water-insoluble products such as finely divided silicon dioxide, pyrogenic silicas, precipitated silicas in hydrophilic or hydrophobic modifications, zeolites, titanium dioxide, cellulose powder, or other fine-particle powders of crosslinked polymers which are different from superabsorbents. The polymerizable aqueous mixtures may contain the thickeners in amounts of up to 30% by weight. If such thickeners are in fact used, they are present in the polymerizable aqueous mixture in amounts of from 0.1, preferably 0.5, to 20% by weight.

In order to optimize the foam structure, it is possible where appropriate to add hydrocarbons with at least 5 carbon atoms in the molecule to the aqueous reaction mixture. Examples of suitable hydrocarbons are pentane, hexane, cyclohexane, heptane, octane, isooctane, decane and dodecane. The suitable aliphatic hydrocarbons may be straight-chain, branched or cyclic and have a boiling point which is above the temperature of the aqueous mixture during the foaming. The aliphatic hydrocarbons increase the pot life of the foamed aqueous reaction mixture which has not yet polymerized. This facilitates the handling of the foams which have not yet polymerized and increases the reliability of the process. The hydrocarbons are used in amounts of from 0 to 10% of the weight of the polymerizable aqueous mixture. When they are used, the amounts preferably present in the aqueous mixture are from 0.1 to 5% by weight.

In order to alter the properties of the superabsorbents, for example the absorption speed and the absorption capacity for water, it may be advantageous to add a polymerization regulator or a mixture of several polymerization regulators to the aqueous reaction mixture. Examples of suitable polymerization regulators are formic acid, thio compounds such as 2-mercaptoethanol, mercaptopropanol, mercaptobutanol, dodecyl mercaptan, thioglycolic acid or amides such as ethanolamine, diethanolamine, triethanolamine, triethylamine, morpholine or piperidine. The amounts of polymerization regulators can be up to 10% of the weight of the monomers used. If polymerization regulators are used, preferably from 0.1 to 5% of the weight of the monomers is used.

The constituents indicated under (g) which are to be used optionally, can be employed singly or in a mixture in the production of the polymers according to the invention. However, the absence of thickeners, foam stabilizers, fillers, cell nucleating agents and polymerization regulators is also possible.

In the production, according to the invention, of water-absorbing, expanded, crosslinked polymers the first stage of the process is foaming of the polymerizable aqueous mixture described above. For this purpose, a gas which is inert to free radicals is dispersed in the form of fine bubbles in the aqueous monomer phase in such a way that a foam is formed. Gas bubbles are introduced into a monomer mixture, for example, using beating, shaking, stirring or whipping devices. It is furthermore possible to produce such foams by gases flowing out of a liquid-covered orifice or by utilizing turbulence manifestations in flows. Finally, it is also possible to use the formation of lamellae on wires or screens for this purpose. These various methods may also be combined with one another where appropriate. Examples of suitable gases which are inert to free radicals are nitrogen, carbon dioxide, helium, neon and argon. Nitrogen is preferably used.

The foam is produced according to the invention separately from the polymerization. The polymerizable aqueous mixture can be foamed, for example, in industrial apparatus known for producing urea/formaldehyde foams, cf. Frisch and Saunders, Polymeric Foams Part II, page 679 et seq. (1973). Foaming of the polymerizable aqueous mixture in the laboratory can most simply take place in a conventional kitchen appliance equipped with whisks. Mechanical generation of foam is preferably carried out in an inert gas atmosphere. Examples of inert gases which can be used are nitrogen, the inert gases and carbon dioxide. The foam is produced by combining all the components of the reaction mixture. The procedure for this is expediently first to dissolve all the water-soluble components in water and only then to add the water-insoluble substances. It may also be advantageous, depending on the process used for mechanical generation of the foam and depending on the initiator present in the polymerizable aqueous mixture, to add the initiator only at the end of the foaming process. The consistency of the mechanically produced foams can be varied in a wide range. Thus, it is possible to produce either foams which flow readily or else rigid foams which can be cut. It is likewise possible to vary the average size of the gas bubbles, their size distribution and their arrangement in the liquid matrix by the selection of the surfactants, the solubilizers, thickeners and foam stabilizers, cell nucleating agents, the temperature and the foaming technique within a wide range so that it is possible in a simple way to adjust the density, open-cell character or wall thickness of the matrix material. The temperatures of the polymerizable aqueous mixture during the foaming process are in the range from $-10$ to $100$, preferably $0$ to $\pm 50°$ C. The temperatures used during the production of the foam are in every case below the boiling point of constituents of the polymerizable aqueous mixture. The foam can also be produced under elevated pressure, eg. 1.5 to 25 bar, but atmospheric pressure is preferred.

An essential advantage of the production, according to the invention, of expanded superabsorbents compared with processes hitherto disclosed for producing such foams is to be regarded as being the obtaining, in the first stage of the process according to the invention, of foamed, polymerizable aqueous mixtures which are stable over a lengthy period, eg. up to 6 hours, so that they can be handled without problems, for example. The expanded mixtures which have not yet polymerized can, for example, be placed in a suitable mold for the subsequent polymerization in order to produce molded articles required for a particular application. Waste foam which is possibly produced on shaping the foamed polymerizable aqueous mixture can be returned directly to the process. The foamed polymerizable material can, for example, be applied in the required thickness to a temporary substrate, which is advantageously provided with a non-stick coating. It is possible, for example, to apply the foam to a substrate with a knife. Another possibility is to introduce the polymerizable expanded aqueous mixture into molds which likewise have a non-stick coating, and to polymerize the foam completely therein.

Since the foamed polymerizable aqueous mixture has a long pot life, this mixture is also suitable for producing composite materials. Thus, for example, the polymerizable foam produced mechanically can be applied to a permanent substrate, eg. sheets composed of polymers (eg. polyethylene, polypropylene or polyamide sheets) or metals, nonwovens, fluff, tissues, woven fabric, natural or synthetic fibers, or to other foams. In the production of composite materials it may in some circumstances also be advantageous to apply the polymerizable foam in the form of particular structures or in layers differing in thickness to a substrate. However, it is also possible to apply the polymerizable foam to fluff layers and to impregnate them in such a way that the fluff is, after the polymerization, an integral constituent of the foam. The foamed polymerizable aqueous mixture obtainable in the first stage of the process can also be shaped to large blocks and polymerized. The blocks can, after the polymerization, be cut or sawn to smaller shaped articles. It is also possible to produce sandwich-like structures by applying a foamed polymerizable aqueous mixture to a substrate, to cover the expanded layer with a sheet, nonwovens, tissues, woven fabrics, fibers or other foams, where appropriate of a material differing from the one used first, and again to apply foam and, where appropriate, to cover with another sheet, nonwovens, tissues, woven fabrics, fibers or other foams. The composite is then subjected to the polymerization in the second stage of the process. However, sandwich-like structures with other foam layers can also be produced.

In the second stage of the process for producing the superabsorbents according to the invention, the foamed polymerizable aqueous mixture is polymerized. The polymerization can take place, depending on the initiator used, by increasing the temperature, by exposure to light, by exposure to electron beams or else by increasing the temperature and exposing to light. The temperature of the foamed polymerizable aqueous mixture can be increased by using all processes customary in industry, for example bringing the foam into contact with heatable plates, exposure of the polymerizable foam to infrared radiation, or heating with microwaves. If relatively thick layers of a foam are to be produced, eg. foams with thicknesses of several centimeters, heating of the polymerizable foamed material by a microwave is particularly advantageous because relatively uniform heating can be achieved in this way.

The polymerization is carried out, for example, from 20 to 180, preferably temperatures in the range from 20 to 100, °C.

When the polymerization is initiated by exposing the foamed polymerizable material to light it is possible to use all conventional light-exposure systems as long as their emission spectrum is suited to the photoinitiator used. When the polymerization is initiated by exposure to light it is advantageous to use a combination of a photoinitiator and a thermal initiator and/or a photoinitiator which can also act as thermal initiator, eg. azo initiators. Since the foam becomes very hot during the polymerization due to the high heat of polymerization, the polymerization reaction takes place particularly fast and efficiently in this way. On initiation by exposure to light, the polymerization temperature is in the range from 0 to 150, preferably 10 to 100, °C.

A considerable advantage of the process according to the invention is to be regarded as the fact that the polymerization takes place with substantial retention of the structure of the foamed polymerizable aqueous mixture, ie. the volume of the polymerizable foam changes negligibly during the polymerization. The polymerization reaction is influenced by the temperature at the start, the initiation technique or the removal of heat. The polymerization temperature is preferably controlled so that boiling of the polymerizable aqueous mixture is avoided. As the polymerization advances, the foam solidifies as a consequence of increasing gel formation. After the polymerization is complete the result is an expanded hydrogel which has a water content of from 30 to 80% by weight. The foam has at least partially an open-cell structure. For the foam to be used as superabsorbent, it is desirable for the residual moisture content to be from 1 to 45, preferably 15 to 35, % by weight. The expanded hydrogel resulting from the polymerization is therefore usually dried. In order to obtain a flexible foam, the foam must have a certain residual moisture content. The water content depends greatly on the density of the foam produced. A higher residual moisture content is necessary as the density increases. An upper limit of 35 to 45% by weight of water may therefore be entirely reasonable. If a mixture with a very high solids content is polymerized, resulting in a foam with a very high density, it may in fact be necessary to moisten the foam further after the polymerization in order to obtain the necessary flexibility.

The foam can be dried by all conventional techniques, for example by heating with a stream of hot gas, by reducing the pressure, by exposure to infrared radiation or by heating with microwaves. Microwaves once again prove to be advantageous in this case for drying large-volume shaped articles.

The process according to the invention results in a superabsorbent foam which is predominantly or at least partially open-celled and which is relatively hard and brittle. However, flexible foams are required for many applications. The relatively hard and brittle foam which is initially obtained can, however, be made flexible. This can take place by using external plasticizers or by internal flexibilization.

External plasticizers are components which are, in addition to the gel-forming components, either added to the reaction mixture before the foaming or applied to the foam subsequently. Examples of suitable plasticizers are hydrophilic and hygroscopic substances. External flexibilization is primarily achieved by the specific setting of a particular residual water content. The flexibilization can furthermore be improved by using, for example, polyols such as glycerol, polyalkylene glycols such as polyethylene glycols or polypropylene glycols, or cationic surfactants. Examples of suitable cationic surfactants are products of the reaction of 1 mol of oleylamine with 5 to 10 mol of ethylene oxide which have been quaternized with dimethyl sulfate, distearyldimethylammonium chloride, lauryltrimethylammonium chloride, cetylpyridinium bromide and ethanolamine esters of long-chain fatty acids such as stearic acid diethanolamine ester, stearic acid monoethanolamine ester and stearic acid triethanolamine ester, which is preferably employed as external plasticizer.

Internal flexibilization of the foam means use of plasticizing components which are incorporated into the gel structure. These may be substances which themselves have unsaturated groups and are present in the polymerization as monomers (b) in the polymerizable aqueous mixture and are also incorporated into the gel structure, or which react with the gel-forming material. The internal plasticizer is intended to reduce the glass transition temperature of the polymer which represents the superabsorbent. Examples of suitable internal plasticizers are olefins, esters of ethylenically unsaturated $C_3$–$C_5$-carboxylic acids and monohydric $C_2$–$C_{30}$-alcohols or polyethylene glycol or polypropylene glycol monoesters of monoethylenically unsaturated $C_3$–$C_5$-carboxylic acids. Monomers (b) which are suitable for internal flexibilization are those which reduce the glass transition temperature of the resulting copolymers with monomers (a), eg. vinyl esters of saturated carboxylic acids containing at least 4 carbon atoms, alkyl vinyl ethers with at least 2 carbon atoms in the alkyl group, vinyllactams and alkyl-substituted styrenes such as ethylstyrene.

As indicated above, an inhomogeneous crosslink density can be produced even during the production of the superabsorbent foams according to the invention. This is particularly advantageous when the monomers used as the components, described above, are (a) acrylic acid, methacrylic acid, vinylsulfonic acid, acrylamidopropanesulfonic acid or mixtures thereof, and (c) a mixture of at least one water-soluble and at least one water-insoluble crosslinker.

It may, nevertheless, be desirable subsequently to alter the degree of crosslinking of the foam. In order to achieve this, for example, it is possible to incorporate latent crosslinkage points in the gel during the polymerization by adding suitable monomers, these points not leading to crosslinking reactions under the conditions of production of the foam but being able under specific conditions which can be applied subsequently, eg. by greatly increasing the temperature, to form further crosslinkage points in the gel structure. Examples which can serve for such monomers are hydroxyl-containing compounds which are able at elevated temperature, ie. above 150° C., to react with the carboxyl groups in the foam structure in which they are incorporated. Examples of compounds suitable as latent crosslinkage points are hydroxyethyl acrylate, hydroxypropyl acrylate, hydroxybutyl acrylate, monoacrylic esters of glycerol, monoacrylates or monomethacrylates of polyethylene glycols with at least 2 ethylene glycol units, monoacrylates or monomethacrylates of polypropylene glycols with at least 2 propylene glycol units and monomethacrylates of polyhydric alcohols, eg. hydroxybutyl methacrylate, hydroxypropyl methacrylate, hydroxyethyl methacrylate or glycerol monomethacrylate.

Another possibility for homogeneous subsequent crosslinking is provided by subsequent addition of crosslinking reagents, ie. compounds which have at least two reactive groups which are able, under suitable conditions, eg. on heating above 70° C., to react with the acidic groups in the expanded hydrogel. In this case it is also possible to achieve, controlled by the depth of penetration of the crosslinker, a modification of the inhomogeneous crosslink density. Suitable crosslinkers form covalent or ionic bonds with the carboxyl groups of the polymer matrix. Suitable crosslinkers are compounds which have at least two functional groups of the same or different types, eg. hydroxyl, amino, quaternary ammonium, isocyanato, epoxy, aziridino, ester or amide groups. Preferred subsequent crosslinkers are polyalcohols such as glycerol or bisepoxides. The application of the crosslinkers to the foamed material can take place, for example, by spraying, dipping or gas-deposition.

The superabsorbent foams according to the invention have a density of, for example, from $10^{-3}$ to 0.9, preferably 0.05 to 0.7, g/cm³. The density of superabsorbent foams is determined by gravimetry. Squares with sides 5 cm long are cut, for example with a sharp knife, out of a uniform foam layer with a defined thickness of from 3 to 5 mm. These samples are weighed, and the resulting weight is divided by the volume calculated from the dimensions.

In order to determine the extractables present in the expanded superabsorbent, a dried and ground foam sample is dispersed in a 0.9% by weight sodium chloride solution, and the dispersion is stirred for 1 hour. The expanded material is then filtered off, and the amount of extractables in the filtrate is determined by titrimetry.

The absorption capacity of the expanded superabsorbent in water per gram of superabsorbent is determined on pieces of foam which have a thickness of 3 mm and each weigh 1 g. The retention is in this case tested by the teabag test. The liquid used in this case is a 0.9% strength sodium chloride solution. 1 g of the expanded material is packed into a teabag which is then closed. The teabag is then immersed in the liquid for a defined time and, after a drip time of 10 minutes, reweighed. To calculate the absorption capacity it is necessary to carry out a blank test in which a teabag without expanded superabsorbent is immersed in the solution, and the weight of the teabag is determined after the drip time of 10 minutes indicated above. The absorption capacity then results from the following relation.

$$\text{Absorption capacity} = \frac{\text{Weight of the teabag with superabsorbent foam} - \text{weight of the teabag in the blank test}}{\text{Weight of the superabsorbent foam}}$$

The retention is determined in the following way: Same procedure as above except that the teabag is centrifuged at an acceleration of 250 g for 3 min in place of the dripping.

$$\text{Retention} = \frac{\text{Weight of the teabag after centrifugation} - \text{weight of the teabag in the blank test}}{\text{Weight of the superabsorbent foam}}$$

The absorption speed (referred to as AS hereinafter) was determined by cutting out, using a sharp knife, rectangular samples weighing 1 g from foam layers with a uniform thickness of 3 mm. These samples were placed in a Petri dish and 20 g of simulated urine were poured on. A stopclock was used to determine the time taken by the foam to absorb the simulated urine completely. The absorption speed (AS) in g/g·sec is calculated from $$AS = 20\ g/[1\ g \times \text{measured time (in sec)}]$$

The uniformity of liquid absorption is also assessed in this test on a 6-point scale. Scores 1–6 have the following meanings:

1: The foam swells homogeneously from the outset.
2: The foam swells homogeneously after a few seconds.
3: The foam swells homogeneously after 30 sec.
4: The foam swells inhomogeneously the whole time but only a small part is affected by this.
5: The foam swells inhomogeneously the whole time but a considerable part is affected by this.
6: The foam swells only on the surface the whole time.

Composition of simulated urine:
The following salts are dissolved in 1 l of distilled water:

2.00 g KCl
2.00 g Na$_2$SO$_4$
0.85 g NH$_4$H$_2$PO$_4$
0.15 g (NH$_4$)$_2$HPO$_4$
0.19 g CaCl$_2$
0.23 g MgCl$_2$

The salts must be anhydrous.

Stability of the foam in the swollen state.

The stability of the swollen material is assessed on the samples obtained in the above test using a 4-point scale. Scores 1–4 mean in this case:

1: The foam can be removed undamaged from the Petri dish and can be flexed through 180° without tearing.
2: The foam can be removed undamaged from the Petri dish.
3: The foam tears on removal from the Petri dish.
4: The foam disintegrates to a heap of gel.

The water-absorbing, expanded, crosslinked polymers described above can be used for all purposes for which expanded superabsorbents described in the literature are employed. They are used, for example, in hygiene articles employed to absorb body fluids and in dressing material for covering wounds. They are suitable, for example, as water-absorbing constituent in diapers, sanitary towels and incontinence articles. They can be employed in the form of composite materials. Expanded superabsorbents can additionally be used as sealing material, as soil improver, as soil substitute and as packaging material. Specific embodiments of articles which contain expanded superabsorbents are described in detail, for example, in WO-A-94/22502. The expanded superabsorbents are additionally suitable for dewatering sludges, for thickening water-based surface coatings, eg. for the disposal of residual amounts of unused water-based surface coatings or paints, by adding, for example, expanded superabsorbents in powder form to water-based surface coating residues until solidification occurs. The expanded, water-absorbing, crosslinked polymers can additionally be used for removing water from oils which contain water. They can be employed, for example, in the form of a powder with an average particle diameter of 150 μm to 5 mm in the applications described above.

The foams described above can, by reason of their properties, carry out various functions in hygiene articles in the storage of body fluids:

acquisition distribution and/or storage

The foams perform the storage of body fluids entirely, whereas other constituents, such as high loft nonwovens, polypropylene nonwovens, polyester nonwovens or chemically modified celluloses, may be used to assist, as layer on the foams, the acquisition and distribution functions.

The percentage data in the examples are percent by weight unless otherwise evident from the context.

EXAMPLES

Example 1

The following components are mixed in a beaker using a magnetic stirrer:

| | |
|---|---|
| 224.20 g | of a 37.3% strength solution of sodium acrylate in water |
| 21.36 g | of acrylic acid |
| 1.05 g | of triacrylic ester of glycerol etherified with 20 ethylene oxide |
| 3.15 g | of adduct of 80 mol of ethylene oxide and 1 mol of tallow fatty alcohol |
| 0.53 g | of 1,4-butanediol diacrylate |
| 4.30 g | of pentane |
| 49.68 g | of water |

The resulting homogeneous mixture is transferred into a 2 l flask into which argon is passed from below. 2 whisks are inserted into the flask, each being connected to a Janke & Kunkel Type RW 20 DZM stirrer. The stream of argon is adjusted so that it bubbles at a rate of 2.5 l/h through the reaction mixture. The two stirrers are initially adjusted to a speed of 60 rpm. 45.00 g of finely ground superabsorbent (particle size <100 μm) are added to the reaction mixture and mixed in homogeneously. The opening of the flask is almost completely sealed with Parafilm, and the stirrer speed is increased to 1000 rpm. The mixture is beaten at this speed and at room temperature for 20 min. 5 minutes before the end of the beating process, 11.9 g of a 3% strength solution of 2,2'-azobis(2-amidinopropane) dihydrochloride are added to the flask. A fine-particle, free-flowing foam is obtained after the end of the beating period.

The foam is introduced in a layer 3 mm thick into a polypropylene box (dimensions: width 20 cm, depth 20 cm, height 15 cm) which has previously been flushed with argon. The foam is exposed to light in this box for 60 sec. The result is a highly flexible foam layer which is uniformly 3 mm thick and can easily be removed from the box. It is dried in a vacuum oven at 70° C. under 20 mbar to a residual water content of 25%. For equilibration, the dried foam layer is stored overnight in a tightly closed polyethylene bag. After this, the resulting foam layer is still soft and flexible. For test purposes, a small piece of the sample is completely dried under reduced pressure.

Properties of the superabsorbent foam:

| | |
|---|---|
| Density: | 650 g/l |
| Extractables: | 5.7% |
| Absorption: | 23.5 g/g |
| Retention: | 10.6 g/g |
| AS: | 1.1 g/g · sec |
| Score for uniformity of absorption: | 1 |
| Score for stability in the swollen state: | 1 |

Example 2

| | |
|---|---|
| Substances used: | 400.00 g of Na acrylate solution (37.3% strength) |
| | 38.10 g of acrylic acid |
| | 2.00 g of trimethylolpropane triacrylate (TMPTA) |
| | 21.22 g of 2,2'-azobis(N,N'-dimethyleneisobutyramidine) dihydrochloride (3% strength aqueous solution) |
| | 10.00 g of Na salt of a C$_{13}$/C$_{15}$ oxo alcohol sulfuric acid half ester |

Firstly the crosslinker (TMPTA) is dissolved in the acrylic acid in a vessel with a screw cap. While stirring, the Na acrylate and the emulsifier are added. The mixture is stirred with a magnetic stirrer for at least 4 hours. The mixture is beaten to a foam at the highest setting in a Bosch kitchen appliance with lid. During this process, the air space above the foam is continuously filled with carbon dioxide. After 15 minutes, the initiator solution is added and beating is continued for 5 minutes. The result is a fine, free-flowing foam with a volume of about 3 liters.

The foam is transferred into a polypropylene mold 15.5×19.0×18.0 cm in size and polymerized in a microwave for 10 minutes.

A foam block 7 cm thick is obtained.

Properties of the superabsorbent foam:

| | |
|---|---|
| Density: | 115.3 g/l |
| Extractables: | 10.4% |
| Absorption: | 57.4 g/g |
| Retention: | 32.9 g/g |
| AS: | >37 g/g · sec |

Example 3

| | | |
|---|---|---|
| Substances used: | 400.00 g | of Na acrylate solution (37.3% strength) |
| | 38.10 g | of acrylic acid |
| | 2.00 g | of trimethylolpropane triacrylate (TMPTA) |
| | 21.22 g | of 2,2'-azobis(N,N'-dimethyleneiso-butyramidine) dihydrochloride (in the form of a 3% strength aqueous solution) |
| | 10.00 g | of Na salt of a $C_{13}/C_{15}$ oxo alcohol sulfuric acid half ester |
| | 10.00 g | of a hydrophilic precipitated silica with an average particle size of 7 μm |

Firstly the crosslinker (TMPTA) is dissolved in the acrylic acid in a vessel with a screw cap. While stirring, the Na acrylate, the emulsifier and the precipitated silica are added. The mixture is stirred with a magnetic stirrer for at least 4 hours. The mixture is beaten to a foam at the highest setting in a Bosch kitchen appliance with lid. During this process, the air space above the foam is continuously filled with carbon dioxide. After 15 minutes, the initiator solution is added and beating is continued for 5 minutes. The result is a fine, stiff foam with a volume of about 3 liters.

The foam is transferred into a polypropylene mold 15.5×19.0×18.0 cm in size and polymerized in a microwave for 10 minutes. A foam block 8 cm thick is obtained.

Properties of the superabsorbent foam:

| | |
|---|---|
| Density: | 87.5 g/l |
| Extractables: | 7.4% |
| Absorption: | 52.3 g/g |
| Retention: | 23.3 g/g |
| AS: | 0.12 g/g · sec |

Example 4

| | | |
|---|---|---|
| Substances used: | 400.00 g | of Na acrylate solution (37.3% strength) |
| | 38.10 g | of acrylic acid |
| | 2.00 g | of trimethylolpropane triacrylate |
| | 21.22 g | of 2,2'-azobis(N,N'-dimethyleneiso butyramidine) dihydrochloride (in the form of a 3% strength aqueous solution) |
| | 10.00 g | of Na salt of a $C_{13}/C_{15}$ oxo alcohol sulfuric acid half ester |
| | 5.00 g | of a hydrophilic precipitated silica with an average particle size of 7 μm |

Firstly the crosslinker (TMPTA) is dissolved in the acrylic acid in a vessel with a screw cap. While stirring, the Na acrylate, the emulsifier and the precipitated silica are added. The mixture is beaten to a foam at the highest setting in a Bosch kitchen appliance with lid. During this process, the air space above the foam is continuously filled with carbon dioxide. After 15 minutes, the initiator solution is added and beating is continued for 5 minutes. The result is a fine, stiff foam with a volume of about 2 liters.

The foam is transferred into a polypropylene mold 15.5×19.0×18.0 cm in size and polymerized in a microwave for 10 minutes. A foam block 7 cm thick is obtained.

Properties of the foam:

| | |
|---|---|
| Density: | 99.1 g/l |
| Extractables: | 9.7% |
| Absorption: | 61.3 g/g |
| Retention: | 31.1 g/g |
| AS: | 0.80 g/g · sec |

Example 5

| | | |
|---|---|---|
| Substances used: | 400.00 g | of Na acrylate solution (37% strength) |
| | 38.10 g | of acrylic acid |
| | 2.00 g | of trimethylolpropane triacrylate |
| | 0.64 g | of 2,2'-azobis(N,N'-dimethyleneiso-butyramidine) dihydrochloride (in the form of a 3% strength aqueous solution) |
| | 10.00 g | of stearic acid triethanolamine ester quaternized with dimethyl sulfate |
| | 2.50 g | of hydroxyethylcellulose (2% strength Brookfield viscosity = 6000 mPas) |

Firstly the crosslinker is dissolved in the acrylic acid in a vessel with a screw cap. While stirring, the Na acrylate, the emulsifier and the hydroxyethylcellulose are added. The mixture is then stirred overnight. The mixture is beaten to a foam for 20 min in a Bosch kitchen appliance with lid. During this process, the air space above the foam is continuously filled with carbon dioxide. After this, the initiator solution is added and beating of the polymerizable mixture is continued for 5 minutes. The result is a fine, stiff foam with a volume of about 2.5 l. The foam is transferred into a polypropylene mold 15.5×19.0×18.0 cm in size and polymerized in a microwave.

A foam block 9 cm thick is obtained.

Properties of the superabsorbent foam:

| | |
|---|---|
| Density: | 76.4 g/l |
| Extractables: | 10.3% |
| Water absorption: | 55.3 g/g |
| Retention: | 42.1 g/g |
| AS: | 1.2 g/g · sec |

Example 6

| | | |
|---|---|---|
| Substances used: | 400.00 g | of 37% strength aqueous Na acrylate solution |
| | 38.10 g | of acrylic acid |
| | 1.87 g | of triacrylic ester of glycerol etherified with 20 mol of ethylene oxide |
| | 0.64 g | of 2,2'-azobis(N,N'-dimethylene-isobutyramidine) dihydrochloride (in the form of a 3% strength aqueous solution) |
| | 10.00 g | of stearic acid triethanolamine ester quaternized with dimethyl sulfate |

A foam is produced by the method indicated in Example 4. A fine, rather stiff foam with a volume of about 3.5 l results. The foam is transferred into a polypropylene mold 15.5×19.0×18.0 cm in size and polymerized in a microwave for 10 minutes. A foam block 8 cm thick is obtained.

Properties of the superabsorbent foam

| | |
|---|---|
| Density: | 84.3 g/l |
| Extractables: | 9.8% |
| Water absorption: | 58.4 g/g |
| Retention: | 43.2 g/g |
| AS: | 1.1 g/g · sec |

Example 7

| | | |
|---|---|---|
| Substances used: | 400.0 g | of 37% strength aqueous Na acrylate solution |
| | 31.8 g | of acrylic acid |
| | 2.0 g | of trimethylolpropane triacrylate |
| | 0.64 g | of 2,2'-azobis(N,N'-dimethyleneiso-butyramidine) dihydrochloride (in the form of a 3% strength aqueous solution) |
| | 8.00 g | of Na salt of a $C_{13}/C_{15}$ oxo alcohol sulfuric acid half ester |
| | 2.00 g | of $C_{15}$-alkylsulfonic acid as Na salt |

The substances indicated above are foamed and polymerized by the method indicated in Example 4. Initially a fine, stiff foam with a volume of 3 l is produced. A foam block 6 cm thick is obtained after the polymerization.

Properties of the superabsorbent foam

| | |
|---|---|
| Density: | 113.0 g/l |
| Extractables: | 9.5% |
| Water absorption: | 54.7 g/g |
| Retention: | 43.2 g/g |
| AS: | 1.3 g/g · sec |

We claim:

1. A water-absorbing, expanded, crosslinked polymer obtainable by
   (I) foaming a polymerizable aqueous mixture consisting essentially of
      (a) a monoethylenically unsaturated monomer which contains an acidic group and which is at least 50 mol % neutralized;
      (b) a crosslinker,
      (c) 0.1–20% by weight of at least one surfactant,
   wherein the foaming takes place by dispersing fine bubbles of a gas inert to free radicals from an external source,
   (II) adding an initiator thereto, and
   (III) polymerizing the foamed mixture to form an expanded hydrogel and adjusting the water content of the expanded polymer to 1–45% by weight.

2. A water-absorbing, expanded, crosslinked polymer as claimed in claim 1, wherein the polymerizable aqueous mixture employed comprises as
   (a) monoethylenically unsaturated monomers which contain acidic groups and are at least 50 mol % neutralized,
   (b) $C_2$–$C_{25}$-olefins, esters of monoethylenically unsaturated $C_3$–$C_5$-carboxylic acids and monohydric $C_2$–$C_{25}$-alcohols, polyethylene glycol or polypropylene glycol monoesters of monoethylenically unsaturated $C_3$–$C_5$-carboxylic acids, vinyl esters of saturated carboxylic acids containing at least 4 carbon atoms, alkyl vinyl ethers with at least 2 carbon atoms in the alkyl group, alkyl-substituted styrenes, hydroxyalkyl esters of monoethylenically unsaturated $C_3$–$C_5$-carboxylic acids, N-vinyllactams, N-vinylimidazoles with 5 to 8 carbon atoms, and their salts and quaternization products, basic esters or amides of monoethylenically unsaturated $C_3$–$C_5$-carboxylic acids, and their salts and quaternization products.

3. A water-absorbing, expanded, crosslinked polymer as claimed in claim 1, wherein the polymerizable aqueous mixture employed consists of
   (a) monoethylenically unsaturated monomers which contain acidic groups and are at least 50 mol % neutralized, and
   (b) a mixture of at least one water-soluble and at least one water-insoluble crosslinker.

4. A water-absorbing, expanded, crosslinked polymer as claimed in claim 1, which comprises 0.1–10% by weight of an external plasticizer from the group of polyols, polyalkylene glycols and cationic surfactants.

5. A water-absorbing, expanded, crosslinked polymer as claimed in claim 1, wherein the entire surface is subsequently crosslinked by impregnating the expanded, crosslinked polymer with crosslinking reagents which have at least 2 reactive groups and react with the acidic groups present in the hydrogel on heating above 70° C.

6. A process for producing a water-absorbing, expanded, crosslinked polymer, consisting essentially of foaming a polymerizable aqueous mixture of (a) a monoethylenically unsaturated monomer which contains an acidic group and which is at least 50 mol % neutralized;

(b) a crosslinker, (c) 0.1–20% by weight of at least one surfactant, in a first stage by dispersing fine bubbles of a gas inert to free radicals from an external source, adding an initiator thereto and polymerizing the resulting foam in a second stage to form an expanded hydrogel, and adjusting the water content of the expanded hydrogel to 1–45% by weight.

7. A process as claimed in claim 6, wherein the monomers used are (a) acrylic acid, methacrylic acid, vinylsulfonic acid, acrylamidopropanesulfonic acid or mixtures thereof, and (c) a mixture of at least one water-soluble and at least one water-insoluble crosslinker.

8. A process as claimed in claim 6 or 7, wherein acrylic and methacrylic esters of at least dihydric alcohols or methylenebisacrylamide are used as water-soluble crosslinkers (c).

9. A process as claimed in claim 6, wherein adducts of ethylene oxide and/or propylene oxide and alcohols containing at least 10 carbon atoms, where the adducts contain from 3 to 200 mol of ethylene oxide and/or propylene oxide per mol of alcohol, are used as surfactants (e).

10. A process as claimed in claim 6, wherein alkali metal or ammonium salts of sulfuric acid half esters of adducts of ethylene oxide and/or propylene oxide and fatty alcohols, alkali metal or ammonium salts of alkylbenzenesulfonic acids or of alkylphenol ether sulfates are used as surfactants (e).

11. A process as claimed in claim 6, wherein quaternization products of tertiary amines or amine esters which contain at least one $C_{10}$–$C_{18}$-alkyl radical are used as surfactants (e).

12. A process as claimed in claim 6, wherein water-swellable or water-soluble synthetic or natural polymers are used as thickeners.

13. A process as claimed in claim 6, wherein superabsorbents in powder form are used as thickeners.

14. A process as claimed in claim 6, wherein aliphatic hydrocarbons whose boiling point is above the temperature of the aqueous mixture during the foamings are used as stabilizers for the foamed aqueous mixtures.

15. The use of the water-absorbing, expanded, crosslinked polymers as claimed in claim 1 in hygiene articles employed to absorb body fluids, in dressing material for covering wounds, as sealing material, as soil improver, as soil substitute and as packaging material.

16. The use of the water-absorbing, expanded, crosslinked polymers as claimed in claim 1 in the form of a powder with an average particle diameter of 150 μm to 5 mm in hygiene articles employed to absorb body fluids, in dressing material for covering wounds, as sealing material, as soil improver and as soil substitute for growing plants.

17. The method of claim 6, further comprising adding at least one polymerization initiator after the first stage and prior to the second stage.

18. The polymer of claim 1, wherein said polymerizable aqueous mixture further contains:

(d) an additional monoethylenically unsaturated monomer, (e) at least one solubilizer and (f) an additive selected from the group consisting of a thickener, a foam stabilizer, polymerization regulator, a filler and a cell nucleating agent.

19. The process of claim 6, wherein said polymerizable aqueous mixture further contains:

(d) an additional monoethylenically unsaturated monomer, (e) at least one solubilizer and (f) an additive selected from the group consisting of a thickener, a foam stabilizer, polymerization regulator, a filler and a cell nucleating agent.

20. The polymer of claim 1, wherein said monoethylenically unsaturated monomer component (a) is present in an amount of from 10 to 80% by weight and said initiator, component (II) is present in an amount of from 0.001 to 5% by weight and said component.

21. The polymer of claim 1, wherein said monoethylenically unsaturated monomer component (a) is present in an amount of from 20 to 60% by weight and said initiator, component (II) is present in an amount of from 0.01 to 2% by weight and said component.

22. The polymer of claim 18, wherein said additional monoethylenically unsaturated monomer is present in an amount of up to 50% by weight based on the polymerizable aqueous mixture.

23. The polymer of claim 18, wherein said additional monoethylenically unsaturated monomer is present in an amount of up to 20% by weight based on the polymerizable aqueous mixture.

24. The method of claim 6, wherein said monoethylenically unsaturated monomer component (a) is present in an amount of from 10 to 80% by weight and said initiator, component (II) is present in an amount of from 0.001 to 5% by weight and said component.

25. The method of claim 6, wherein said monoethylenically unsaturated monomer component (a) is present in an amount of from 20 to 60% by weight and said initiator, component (II) is present in an amount of from 0.01 to 2% by weight and said component.

26. The method of claim 19, wherein said additional monoethylenically unsaturated monomer, component (d) is present in an amount of up to 50% by weight based on the polymerizable aqueous mixture.

27. The method of claim 19, wherein said additional monoethylenically unsaturated monomer, component (d) is present in an amount of up to 20% by weight based on the polymerizable aqueous mixture.

28. The polymer of claim 1, wherein said expended polymer is predominantly or partially open-celled.

29. The process of claim 6, wherein said expanded hydrogel is predominantly or partially open-celled.

* * * * *